(12) United States Patent
Giraldo Cadavid et al.

(10) Patent No.: US 10,736,500 B2
(45) Date of Patent: Aug. 11, 2020

(54) SYSTEM AND METHOD FOR MEASURING SENSORY RESPONSE OF TISSUE

(71) Applicant: UNIVERSIDAD DE LA SABANA, Chia, Cundinamarca (CO)

(72) Inventors: Luis Fernando Giraldo Cadavid, Cundinamarca (CO); Luis Mauricio Agudelo Otálora, Cundinamarca (CO); Mario Arbulú Saavedra, Cundinamarca (CO); Javier Burguete, Navarra (ES); Secundino Fernandez González, Navarra (ES)

(73) Assignee: UNIVERSIDAD DEL A SABANA, Chia, Cundinamarca (CO)

( * ) Notice: Subject to any disclaimer, the term of this patent is extended or adjusted under 35 U.S.C. 154(b) by 958 days.

(21) Appl. No.: 14/537,288

(22) Filed: Nov. 10, 2014

(65) Prior Publication Data
US 2015/0305610 A1    Oct. 29, 2015

Related U.S. Application Data

(63) Continuation-in-part of application No. PCT/IB2014/061063, filed on Apr. 28, 2014.

(51) Int. Cl.
*A61B 1/267* (2006.01)
*A61B 1/05* (2006.01)
(Continued)

(52) U.S. Cl.
CPC .......... *A61B 1/267* (2013.01); *A61B 1/00009* (2013.01); *A61B 1/00045* (2013.01);
(Continued)

(58) Field of Classification Search
CPC . A61B 1/267; A61B 1/00009; A61B 1/00045; A61B 1/00119; A61B 1/015;
(Continued)

(56) References Cited

U.S. PATENT DOCUMENTS 5,261,404 A * 11/1993 Mick .................. A61B 1/00048
128/916
5,436,655 A * 7/1995 Hiyama ............. A61B 1/00193
348/139

(Continued)

FOREIGN PATENT DOCUMENTS

| | | |
|---|---|---|
| CN | 202168826 U | 3/2012 |
| EP | 0444594 A1 | 9/1991 |
| WO | 02091916 A1 | 11/2002 |

OTHER PUBLICATIONS

"International Search Report", PCT International Search Report (dated Nov. 28, 2014), PCT/IB2014/061063, 7 pgs.
(Continued)

*Primary Examiner* — Timothy J Neal
*Assistant Examiner* — William B Chou
(74) *Attorney, Agent, or Firm* — Lucas & Mercanti, LLP

(57) ABSTRACT

A system for measuring sensation or sensory responses of a tissue of a subject (or patient) by delivering air pulses of controlled pressure, duration, and frequency to the tissue surface. The system can include an endoscope having a range finder component to determine the distance between the distal end of the endoscope and a target tissue surface. When it is determined that the endoscope has been positioned at a predetermined distance from the tissue surface, the air pulses can be administered to the tissue surface.

26 Claims, 8 Drawing Sheets

(51) Int. Cl.
*A61B 1/07* (2006.01)
*A61B 1/015* (2006.01)
*A61B 5/00* (2006.01)
*A61M 13/00* (2006.01)

(52) U.S. Cl.
CPC .......... *A61B 1/00119* (2013.01); *A61B 1/015* (2013.01); *A61B 1/05* (2013.01); *A61B 1/0676* (2013.01); *A61B 1/07* (2013.01); *A61B 1/273* (2013.01); *A61B 5/0053* (2013.01); *A61B 5/6846* (2013.01); *A61B 1/00096* (2013.01); *A61B 1/063* (2013.01); *A61B 5/0084* (2013.01); *A61B 5/4205* (2013.01); *A61B 5/682* (2013.01); *A61M 13/003* (2013.01)

(58) Field of Classification Search
CPC ........... A61B 1/05; A61B 1/0676; A61B 1/07; A61B 1/273; A61B 5/0053; A61B 5/6846
USPC ................ 600/109, 129, 156, 158, 159, 160
See application file for complete search history.

(56) References Cited

U.S. PATENT DOCUMENTS

| | | | |
|---|---|---|---|
| 5,970,978 A | 10/1999 | Aviv et al. | |
| 6,036,655 A | 3/2000 | Aviv et al. | |
| 8,033,825 B2* | 10/2011 | Rizoiu | A61C 17/02 433/29 |
| 2004/0220644 A1* | 11/2004 | Shalev | A61N 1/0546 607/45 |
| 2005/0187546 A1* | 8/2005 | Bek | A61B 18/1492 606/41 |
| 2008/0312712 A1* | 12/2008 | Penner | A61N 1/36007 607/40 |
| 2011/0245606 A1* | 10/2011 | Hayashi | A61B 1/015 600/109 |
| 2016/0081591 A1* | 3/2016 | Lever | A61B 5/1104 600/529 |
| 2017/0007324 A1* | 1/2017 | Kadamus | A61M 25/04 |

OTHER PUBLICATIONS

Aviv; et al., "Laryngopharyngeal sensory discrimination testing and the laryngeal adductor reflex", Ann Otol Rhinol Laryngol (Aug. 1999), 108(8):725-30.

Hammer, "Design of a new somatosensory stimulus delivery device for measuring laryngeal mechanosensory detection thresholds in humans", IEEE Trans Biomed Eng (Apr. 2009), 56(4):1154-9.

Willging: et al., "Pediatric FEESST: fiberoptic endoscopic evaluation of swallowing with sensory testing", Curr Gastroenterol Rep (Jun. 2005), 7(3):240-3.

* cited by examiner

SYSTEM AND METHOD FOR MEASURING SENSORY RESPONSE OF TISSUE

REFERENCES TO RELATED APPLICATIONS

This application is a continuation-in-part of International Application PCT/IB2014/061063, filed Apr. 28, 2014, which claims priority to Colombian Application No. 13-121843, filed May 17, 2013, the disclosure of each of which is incorporated by reference herein in its entirety.

BACKGROUND

The pharynx is a structure that connects the digestive and respiratory tracts. It makes up the part of the throat situated immediately posterior to the nasal cavity, posterior to the mouth and superior to the esophagus and larynx. The human pharynx is conventionally divided into three sections: the nasopharynx, the oropharynx and the laryngopharynx. The proper functioning of pharynx and its neighboring structures within the larynx, base of tongue, soft palate and upper esophagus, ensures that the bolus is transported correctly from the mouth into the esophagus without entering the airway and that the air is breathed in and out free of the digestive tract.

The proper functioning of the pharyngeal and laryngeal reflexes is crucial for swallowing and breathing to work without interference between them. The laryngeal adductor reflex, swallowing reflex and cough reflex are major reflexes involved in regulating these processes. The laryngeal adductor reflex, which involves the adduction of the vocal cords, is triggered by mechanical and chemical stimuli of the pharyngeal-laryngeal mucosa and protects against the entry of food and foreign material into the lower respiratory tract. The swallowing reflex is triggered by mechanical and chemical stimuli in the lining of the base of the tongue and pharynx, and generates synchronous contraction or relaxation of different muscle groups of the tongue, soft palate, pharynx, larynx and esophagus for food to pass quickly from the mouth into the esophagus without entering the airway. If food or liquid enters the airway, it may enter the lungs and allow harmful bacteria to grow, resulting in a lung infection called aspiration pneumonia. The cough reflex serves as protection against possible failures in the above reflex mechanisms where food has been allowed entry into the airway. The cough reflex is triggered by mechanical or chemical stimuli on the laryngeal or tracheal mucosa and allows the removal of the material that has entered the airway.

To establish the parameters of swallowing disorder, it is useful to perform examinations of these reflexes. For example, Aviv et al. introduced an apparatus and procedure to clinically examine the sensory thresholds of the laryngeal adductor reflex by air pulses, as described in U.S. Pat. No. 5,970,978, the disclosure of which is incorporated by reference herein in its entirety. This testing of Aviv was known as "Fiberoptic Endoscopic Evaluation of Swallowing with Sensory Testing (FEES-ST)."

In concordance studies, it has been observed that intra-observer reproducibility of the FEES-ST reflex testing is good in experienced operators of the apparatus, but poor in inexperienced hands. The inter-observer reproducibility is poor both between experienced observers and inexperienced observers. Tests performed by experienced observers regarding the sensation threshold changes in pharyngeal and laryngeal reflexes can be useful to predict outcomes, such as penetration, aspiration, and pneumonia. However, good predictions cannot always be made due to unreliable reproducibility of the tests.

It is noted by the current inventors that the problems that compromise the reproducibility of the FEES-ST sensory test may be related to factors that induce variation in the pressure of air pulses over the laryngeal mucosa. Further, the pressure of air pulses over the laryngeal mucosa may vary considerably due to (often unnoticed) changes in the distance from the tip of the endoscope to the site of impact as well as the angle at which the pulses of air strike the mucosa. The air pulses can easily change during the exploration of the reflex, particularly by inexperienced observers, due to patient movement as a result of discomfort or due to difficulties or personal differences in the estimate of the distance or angle of impact. Furthermore, the variations in the actual air pulses delivered to the mucosa could be due to the variability in the air supply sources, such as compressors of different specifications and air channels or tubes of the endoscope for delivering the air pulses which may have different length, material, and/or diameters.

There is a need for an improved design for the apparatus to make sensory thresholds measurements more precise to improve the intra and inter-observer reproducibility and to allow for more reliable diagnosis of patient conditions relating to the airway or digestive tract.

SUMMARY OF THE INVENTION

The purpose and advantages of the disclosed subject matter will be set forth in and apparent from the description that follows, as well as will be learned by practice of the disclosed subject matter. Additional advantages of the disclosed subject matter will be realized and attained by the methods and systems particularly pointed out in the written description and claims hereof, as well as from the appended drawings.

To achieve these and other advantages and in accordance with the purpose of the disclosed subject matter, as embodied and broadly described, one aspect of the disclosed subject matter is directed to a system for delivering a fluid to a surface of a tissue of a subject. The system comprises an endoscope having a distal end and including a range finder component configured to capture images of a surface of a tissue of a subject for determining a distance from the distal end of the endoscope to the surface, a working channel for delivering a fluid from the distal end of the endoscope to the surface of the tissue, and a port for receiving the fluid into the working channel. The system also includes a pressure regulator and a solenoid valve serially coupled to a line of a fluid supply that connects a fluid source to the port of the endoscope, as well as a controller operatively coupled to and controlling each of the pressure regulator and the solenoid valve.

The fluid can be air or other gases, or a liquid, such as water. When the fluid is air, the controller can be configured to control the pressure of air supplied into the working channel by controlling the pressure regulator. The controller can be configured to also control a duration of the air entering into the working channel by controlling the open status of the solenoid valve. The system can include a buffer air tank coupled to the line of the air supply at a location upstream to the pressure regulator, and can further include a manometer coupled to the line of the air supply at a location upstream to the buffer air tank for controlling the pressure of air entering into the buffer tank.

The range finder component can include a laser emitting component configured to project a laser light onto a target location in an area of the tissue surface, and an image capture component configured to capture an image of the area of the tissue surface. In one embodiment, the image capture component can include a lens disposed at the distal end of the endoscope, a remotely disposed image sensor, and a fiber optic connecting the lens and the image sensor, wherein the image sensor is configured to convert optical signals received by the lens and transmitted via the fiber optic into electrical signals. In one embodiment, the laser emitting component comprises a fiber optic for transmitting a laser light from a remotely disposed laser generator.

In one embodiment, the system can further include a lighting component configured to illuminate an area of a tissue surface. The lighting component can include a lens disposed at the distal end of the endoscope and a fiber optic connecting the lens to a remotely disposed illumination light source.

In one embodiment, the fiber optic for transmitting the laser light can be placed in a channel of the endoscope other than the working channel. In other embodiments, the fiber optic for transmitting the laser light can be placed within the working channel, or outside a tubular portion of the endoscope and attached to the sheath of the tubular portion.

In one embodiment, the controller is in operative communication with a computing device which includes a display, a processor and a non-transitory computer readable medium storing instructions, which when executed by the processor, provides a user interface on the display. The user interface can include one or more control elements to allow a user to enter one or more parameters as control commands to be sent to the controller. For example, the user interface can include control elements for a user to enter parameters of the controller for controlling the pressure regulator and the solenoid valve.

In one embodiment, the system further includes a pressure sensor for measuring a pressure of the fluid exiting from the distal end of the working channel of the endoscope. The pressure sensor can be operatively coupled with the controller and outputs the measured pressure to the controller. The user interface can be configured to display the pressure measured by the pressure sensor and retrieved from the controller.

In one embodiment, the computing device contains software component to enable the computing device to send command signals to the controller, the command signals enabling the controller to control the pressure regulator and the solenoid valve to deliver a plurality of fluid pulses having predetermined pressures, durations, and frequencies to the surface of the tissue according to a preset schedule.

In one embodiment, the computing device computes the distance from the distal end of the endoscope to the surface of the tissue by: constructing a digital image based on the electric signals retrieved from the image sensor, the digital image having a visual field having a center; identifying a laser spot produced by the projected laser light in the digital image; calculating a distance on the digital image from the center of the visual field to the center of the laser spot; and based on the calculated distance, deriving the distance from the distal end of the endoscope to the tissue surface. Deriving the distance can include using a regression equation obtained from a prior calibration which correlates the position of a laser spot as shown in an image taken by the image capture component of the endoscope and a measured distance from the end of the endoscope to a test surface.

In another aspect, the present invention provides methods of measuring a sensory response as well as a sensory discrimination threshold of a tissue of a body cavity of a subject. Various embodiments of the system described herein can be used in performing the method. In the methods, the distal end of the endoscope is inserted into the subject to approach a target location of the tissue surface. The distance between the distal end of the endoscope and the target location can be calculated by the computing device in real time (e.g., by a method described above), which allows the user to determine whether the distal end of the endoscope is within a predetermined distance range from the target location of the tissue surface. When that distance reaches the desired range, air pulses of controlled pressures, durations, and frequencies can be delivered through the working channel of the endoscope to the target tissue surface. Based on the observed response of the target tissue to the delivered air pulses, determining the sensory discrimination threshold of the tissue.

Before performing a test to a patient, the pressure of the air to be delivered can be calibrated using a pressure sensor placed at a distance within the predetermined distance range from the distal end of the endoscope. The calibration can include obtaining a correspondence between a pressure as measured by the pressure sensor and a voltage required by the pressure regulator to produce such a pressure measured by the pressure sensor. In one embodiment, the regression equation is an exponential equation. In one embodiment, the computing device is configured to display a polar grid on a display of the computing device that comprises circularly arranged scales indicating estimated distances from the distal end of the endoscope to the surface.

The tissue of the body cavity can be a portion of an airway of the subject, such as a pharyngeal, laryngopharyngeal, or nasopharyngeal portion of the airway of the subject. The tissue of the body cavity can also be a portion of a digestive tract of the subject.

In another aspect, the present invention provides a system for determining a distance from an endoscope to a surface, which includes an endoscope having a distal end. The endoscope includes a laser emitting component configured to project a laser light onto a target location in an area of the surface, and an image capture component. The image capture component can include a lens disposed at the distal end of the endoscope for capturing optical signals of the area of the surface, a remotely disposed image sensor, and a fiber optic connecting the lens and the image sensor. The image sensor is configured to convert optical signals received by the lens and transmitted via the fiber optic into electrical signals. The system can further comprise a computing operatively coupled to the image sensor and configured to perform the distance calculation according to the methods described herein.

BRIEF DESCRIPTION OF THE DRAWINGS

The disclosed subject matter will be more fully understood by reference to the following figures.

It is noted that the figures are not necessarily drawn to scale and certain dimensions have been exaggerated for clarity.

While the disclosed subject matter is capable of various modifications and alternative forms, specific embodiments thereof have been depicted in the figures, and will herein be described in detail. It should be understood, however, that the figures are not intended to limit the subject matter to the particular forms disclosed but, to the contrary, the intention is to illustrate and include all modifications, equivalents, and alternatives within the spirit and scope of the subject matter as defined by the appended claims.

DETAILED DESCRIPTION

The present invention provides a system for measuring sensation or sensory responses of a tissue of a subject (or patient) by delivering fluid pulses of controlled pressure(s), duration(s), and frequency (or frequencies) to the tissue surface. The measurements can be used to evaluate or diagnose a condition relating to the sensation, such as a sensory threshold which may provide insights into disorders of various reflexes of the patient. The tissue can be of a portion of the patient's airway, such as the larynx and the pharynx tract of a patient, or of a portion of the patient's digestive tract, or another tissue in a body lumen/tract or cavity or a skin of the patient which is innervated and able to produce an observable response in reaction to applied fluid pulses. In another aspect, the present invention provides a method of using the system in performing sensation measurements.

Air is used as an example fluid throughout the application, but it is understood that the fluid can be another gaseous substance, such as air or other nontoxic gases such as carbon dioxide, oxygen, nitrogen, etc., or a liquid, such as water.

Figure 1A:
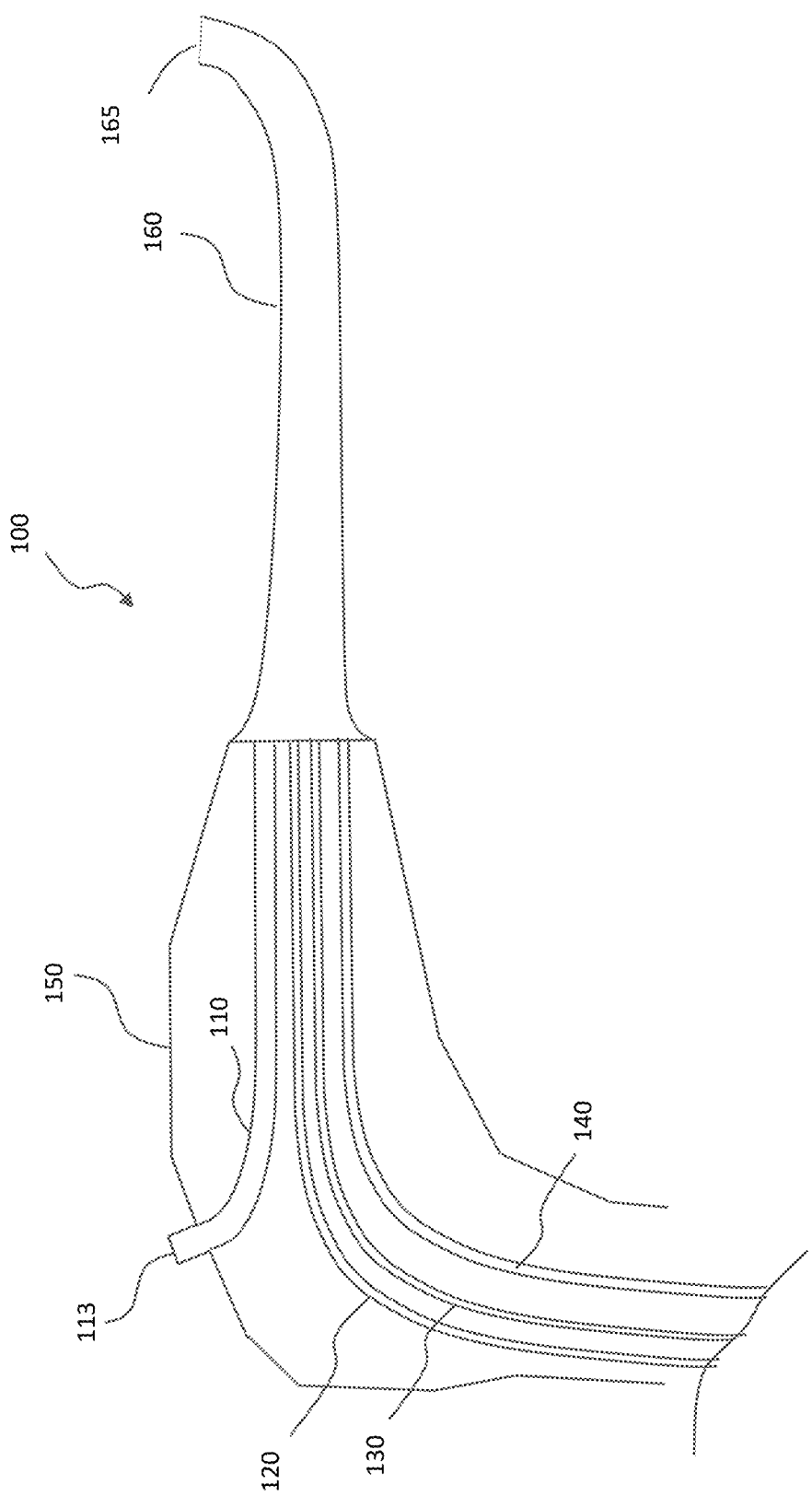
FIG. 1A shows a schematic view of an endoscope in a system for delivering fluid to a tissue of a subject, according to one embodiment of the present invention.

According to one embodiment of the present invention, and referring to FIG. 1A, the system includes an endoscope 100. The endoscope 100 has a body portion 150 and a flexible and generally tubular portion 160 having a distal end 165 (which is also referred to the distal end of the endoscope). The endoscope has a working channel 110 for delivering air from the distal end 165 to a tissue surface. The working channel 110 is in fluidic connection with a port 113 of the endoscope for receiving air from an external air supply. Optical fibers (or fiber optics) 120, 130, and 140 are received in the body 150 of the endoscope, and each extends to the distal end 165. The connection and functionalities of these fiber optics are further described in FIG. 1B.

Figure 1B:
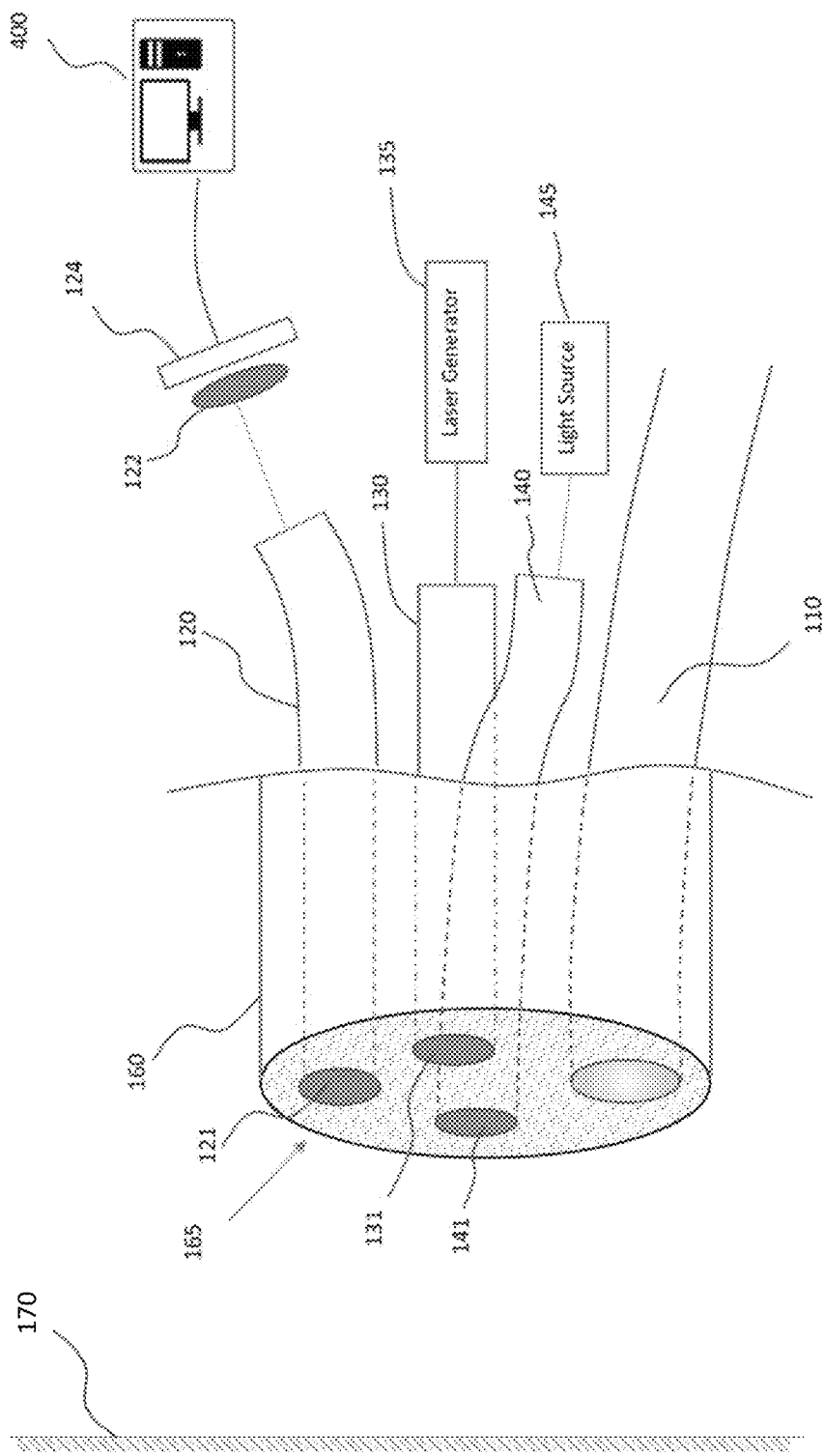
FIG. 1B illustrates an example arrangement of certain components of the endoscope depicted in FIG. 1.
Figure 2:
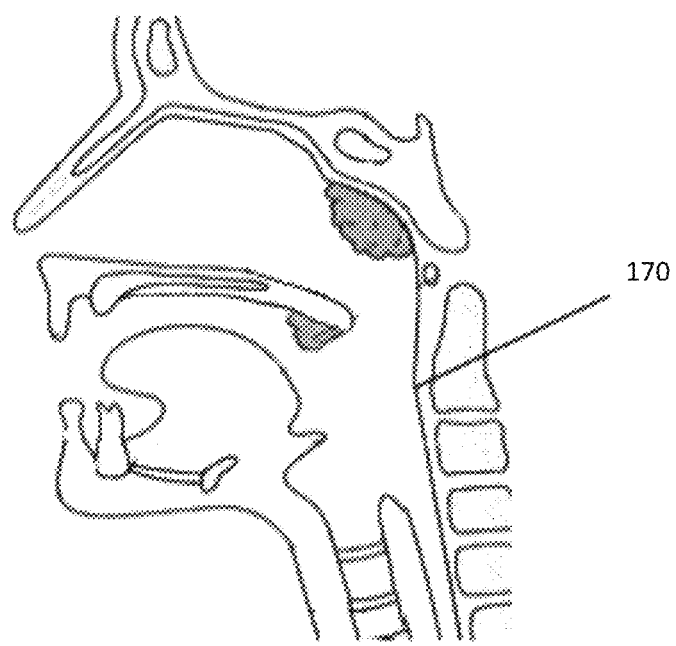
FIG. 2 illustrates a location in the pharyngeal laryngeal tract of a patient for measuring sensory thresholds of the patient.

As shown in FIG. 1B, a lens 121 is disposed at the distal end of the endoscope 165 and in front of the fiber optic 120. The lens 121 captures optical signals of an area of tissue surface 170 (which can be a portion of the pharyngeal laryngeal tract of the patient, as depicted in FIG. 2), and the fiber optic 120 carries the optical signals to a remotely disposed image sensor 124, which converts the optical signals into electric signals. Before reaching the image sensor 124, the optical signals transmitted via optical fiber 120 can be collimated by another lens 122 (the image sensor 124 and the lens 122 together can be a part of a digital camera system). The image sensor 124 can be a CMOS or CCD sensor, or other optoelectronic sensors known in the art. The lens 121, optical fiber 120, and image sensor 124 together forms an image capture component of the endoscope.

Optical fiber 130 is coupled with a remotely disposed laser generator 135 (which can be a laser diode, as will be discussed hereinafter) and transmits laser light to the distal end of the endoscope 165, where the laser light is projected to the tissue surface 170 to form a laser spot or laser dot. A collimator lens 131 can be positioned in front of the end of the fiber optic 130 to further focus the laser light to reduce the size of the laser spot. These elements relating to generating, transmitting, and projecting laser light together forms a laser emitting component for the endoscope.

The laser emitting component and the image capture component together can form a range finder component. Further, image sensor 124 is operatively connected to an external computing device 400, which is equipped with the necessary hardware and software components to perform image analysis to determine the distance from the distal end of the endoscope to the tissue surface based on the position of the laser spot relative to the center of the visual field as captured by the image capture component, as will be further described herein.

For endoscopic applications where the tissue surface is in an internal tract or cavity of the patient, a lighting component for illuminating the tissue surface can be included. As shown in FIG. 1B, the lighting component can include a fiber optic 140 coupled with a light source 145 (e.g., a lamp, a white light LED or the like, or other illumination sources as appropriate), the fiber optic 140 transmitting a visible light (e.g., a white light) from the light source to the distal end of the endoscope 165, where the light is projected to the tissue surface 170 via a lens 141. More than one lighting component can be included in the endoscope as needed or desired, e.g., to provide illumination lighting from more than one location of the distal end of the endoscope to allow for a better visual image of the target surface.

It is understood that the relative positioning of the optical fibers 120, 130, 140 and the working channel 110 in the tubular portion of the endoscope is only illustrative; alternative arrangements can be made. While the optical fiber 130 for transmitting laser light is depicted as being received in a separate channel of the endoscope other than the working channel, the optical fiber 130 can also be positioned within the working channel (while still leaving space for the fluid to flow through), or positioned outside of the sheath (and attached to the sheath) of the tubular portion 160.

Figure 3A:
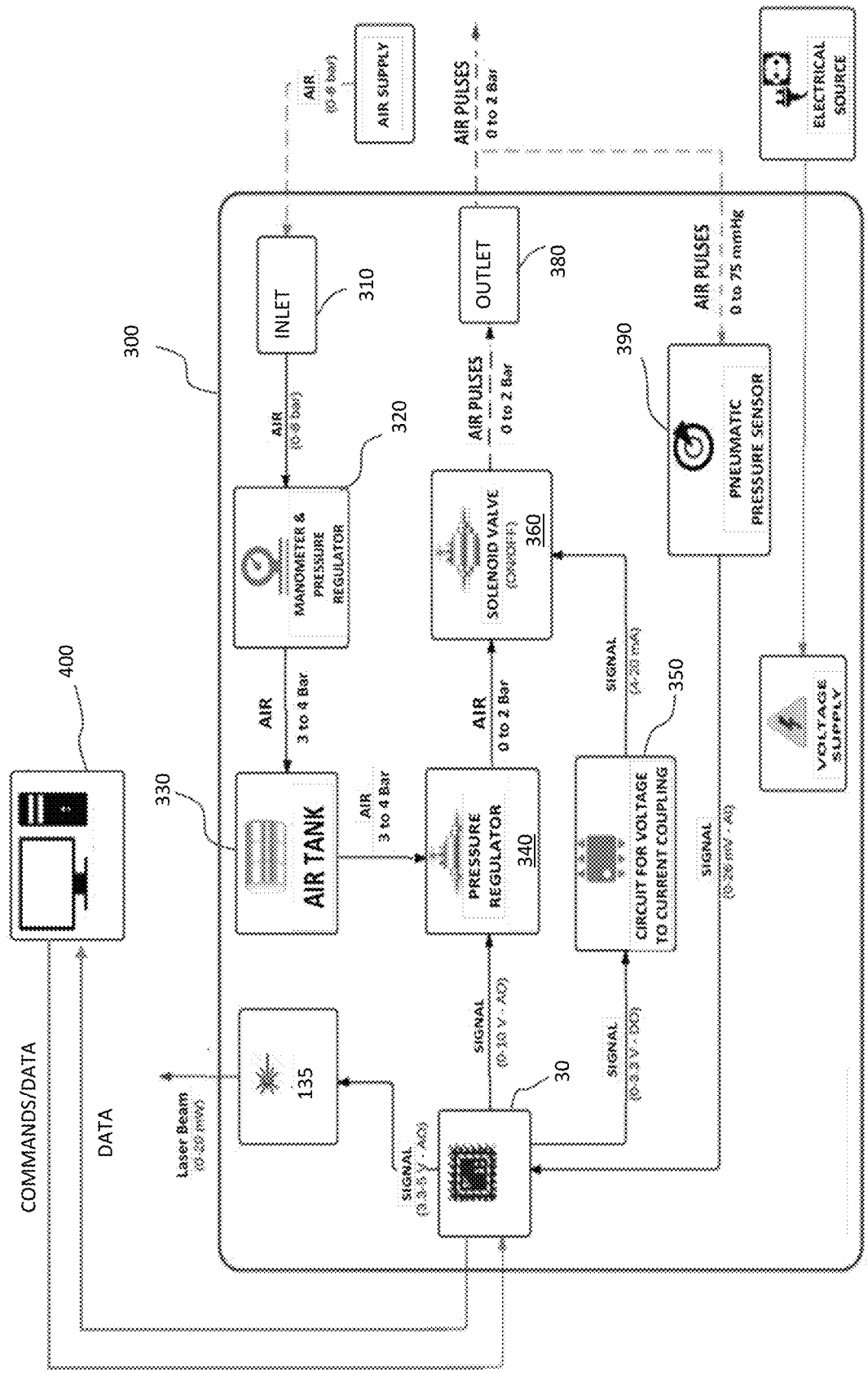
FIG. 3A is a diagram schematically depicting a process and control components for delivering air pulses according to one embodiment of the present invention.
Figure 3B:
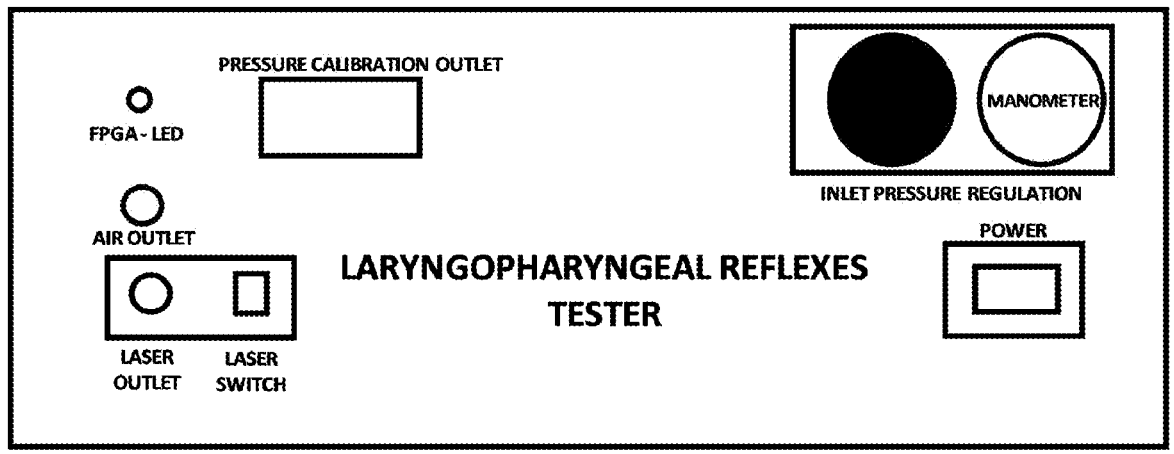
FIG. 3B is a photo of a front view of a device containing various control components for delivering air pulses, according to one embodiment of the present invention.

FIG. 3A is a diagram schematically depicting a process and control components used in the process for delivering air pulses according to one embodiment of the present invention. The various components for the air pulses delivery can be housed in a container unit 300. A front view of the container unit is shown in FIG. 3B. The components in the container can be provided by a voltage supply located in the container. Air is provided initially by an external air supply via an inlet 310, regulated by a manometer 320 before entering a buffer air tank 330, which then supplies air downstream, regulated by an electric pressure regulator 340 and solenoid valve 360. Regulated air pulses of predetermined pressure, duration, and frequency are then sent out, e.g., to the working channel of the endoscope via a port of the endoscope (as shown in FIGS. 1A and 1B).

The electrical connections are centralized in controller 30, which is wired and programmed to provide data acquisition and control functionalities for various components connected thereto, for example, for controlling the operation of pneumatic regulator 340 (e.g., its operating voltage, which determines the opening of the regulator valve), the solenoid valve 360 (e.g., its on/off status, which allows or disallows air to flow downstream), the power for the laser generator 135, and for data capturing from the pressure sensor 390.xxx The controller 30 is also in operative communication with a computing device 400 via wired or wireless data link or links (e.g., Ethernet links or other links) for sending data to and receiving data or control commands from the computing device (via a user-machine interface, as will be described further below). For example, a LabVIEW 2013 based program responsible for reading and writing of digital and analog outputs and inputs can be embedded in the controller 30. In a specific embodiment, the specifications/description of various components as depicted in FIG. 3 are provided in the Table below.

| Controller: NI sbRIO 9636 | National Instruments | Processor of 400 MHz. 512 MB of nonvolatile storage. 256 MB DRAM. FPGA Xilinx Spartan-6 LX45 reconfigurable for timing. 16 analog inputs of 16-bit from −10 to 10 V. Sampling rate of the analog inputs of 200 KS/s 4 analog outputs of 16 bits from 0 to 10 V. 28 DIO lines of 3.3 V. Ethernet ports 10/100 BASE-T, serial RS232, serial RS485 y USB. Environmental and local temperature operating range of −40 a 85° C. Supply voltage of 9 to 30 V DC. | Data acquisition card (DAQ), with analog and digital inputs and outputs, for controlling the pneumatic valves, the laser module and the pressure sensor for calibration. |
|---|---|---|---|
| Pressure Regulator: VPPE-3-1/8-2-010 E1 557771 | FESTO | Operating environment: unlubricated filtered air (40 μm). Permitted supply pressure (input pressure): 2 to 3 Bar. Control range (output pressure): 0.02 to 2 bar Flow rate of 400 nl/min at 2 bar. Connecting plug M12 of 4-pin. Setpoint value 0 to 10 V. Nominal current 0.05 A. Max. current 0.15 A. Supply Voltage 24 V DC. | Proportional pressure regulator used to reach the desired air-pulse pressure. |
| Solenoid Valve: MHA1-M1H-3/2O-0,6-HC | FESTO | Supply voltage 24 V DC. Input pressure 0 to 8 bar. Temperature range: −5 a 40° C. Power consumption: 1.1 W. Maximum switching frequency: 20 Hz. Normally closed valve. Operating medium: Filtered compressed air, lubricated or unlubricated, grade of filtration 40 μm. Response time on/off: 4 ms. Electrical signal: 4 a 20 mA. Flow rate 10 l/min. | Electrical solenoid valve, miniature, for fast on/off, allows air pulses of at least 10 ms and frequencies up to 20 Hz. |
| Pressure Sensor: MPX2010GSX | FREESCALE Semiconductor | Pressure measurement range: 0 to 10 KPa (0 to 75 mmHg). Supply Voltage: 10 to 16 V DC. Supply Current: 6 mA DC. | Piezoresistive pressure sensor for measuring the output pressure of the system. It will be used to callibrate the output pressure. |

-continued

| | | | |
|---|---|---|---|
| | | Ouput voltage range (Full Scale Span): 0 to 26 mV DC, at 25° C. of temperature. | |
| Laser Generator: FTEC2532-V10TA0 | BLUE SKY RESEARCH | Input Voltage: 5 to 6.5 V DC. Laser Power regulation by analogue input from 3.3 to 5 V DC. Maximum laser power 10 mW. Laser Wavelength: 532 nm (green). | Fiber Coupled Diode Laser Module It is used for the laser range-finder and sight through specific software. |
| MANOMETER AND PRESSURE REGULATOR | FESTO | Operating environment: inert gas and neutral fluids. Maximum pressure: 10 Bar. Output pressure: 0 to 10 Bar. | Manometer and pressure regulator to regulate the input pressure to the electronic pressure regulator. Guarantees that the supply pressure of the electronic pressure regulator be in the range of 3 to 4 Bar. |
| AIR VOLUME TANK AVT-24-8 | CLIPPARD MINIMATIC | Maximum pressure: 17 Bar. | Pneumatic reserve tank. Used to guarantee a steady supply pressure to the solenoid valve. |
| Electric Foot Pedal(s) Switch Type | | Voltage supply: 0 or 3.3 V. | Switch to start, restart, stop, pause or continue the administration of air pulses. |

The control mechanisms of some of these components are illustrated below. An analog signal that varies between 0 and 10 V DC is sent from the controller 30 (DAQ) for the pressure regulator VPPE-3-1/8-2-010 E1 557771, as configured in the user-machine interface on the computing device 400, generates a proportional passage of air according to the operating voltage. The DAQ also generates a signal of 0 to 3.3 V DC for the solenoid on/off valve (MHA1-M1H-3/20-0,6-HC). This signal passes through a coupling circuit 350 that changes the voltage signal into a current signal of 4 to 20 mA, which can be maintained for a period of 50-1000 ms according to the user interface configuration. This can be established when starts and ends each air-pulse. The DAQ also sends an analog signal of 3.3 to 5 V DC which allows the regulation of the intensity of the laser light emitted by the laser generator (laser diode FTEC2532-V10TA0), which increases power in proportion to the drive voltage to reach a maximum of 20 mW at a 5V signal. The DAQ can record the data issued by the pressure sensor MPX2010GSX at a sampling rate of 200 KS/s for calibrating the output pressure according to the needs of the test.

The pneumatic flow passes through a manometer 320 which enables the regulation of the air entering the system according to the high precision digital air pressure regulator specifications (3 to 4 bar). The buffer air tank 330 cushions the shock of input pressure and ensures that the system always has the required amount of air and pressure (3 to 4 bar). The air then reaches the pressure regulator VPPE-3-1/8-2-010 E1 557771, which regulates the air passage as configured in the user interface of the computing device 400 to achieve the selected pressure (from 0.00133 to 0.0133 bar or 1-10 mm Hg). The fast on/off solenoid valve (MHA1-M1H-3/20-0,6-HC) regulates the duration and frequency of the air pulses (from 50-1000 ms for opening and 50-3000 ms for closing times). Finally, the air pulses exit from the outlet 380 to be delivered by the endoscope to the patient subjected to the sensory measurement or may be delivered to the pressure sensor 390 (MPX2010GSX) for calibration.

The computing device 400 can be a workstation, a desktop computer, a laptop, a tablet, or other computing devices that include a memory and a processor and a software component to enable the computing device to communicate with and control the controller 30, e.g., retrieving data from controller 30 and displaying the working parameters and status of the various components controlled by the controller 30 (e.g., pressure regulator 340, solenoid 360, laser generator 135, etc.), and sending data/commands to controller 30 to control the operations of these components. The computing device 400 can include a display, and the software component, when executed, can provide a user-machine interface (or user interface) on the display which includes one or more user control elements to allow a user to enter one or more parameters as control commands to be sent to the controller. The user interface can also display values, parameters, or data retrieved from the controller 30 that indicate the status of the various components. Additionally, the user interface can further include an area for displaying live images of the tissue surface as captured by the image capture component of the endoscope.

To perform an examination of sensory response of a surface of a tissue of a patient, the distal end of the endoscope of the system can be introduced to a position near the target tissue surface, then it is determined, by a software component implemented in the computing device, whether the distance from the distal end of the endoscope to the target tissue surface is within a predetermined distance range. For example, for determining the sensory discrimination threshold of the pharyngeal reflex, the predetermined range can be about 8 mm to 10 mm, e.g., 9 mm. Once the endoscope is properly positioned, air pulses of predetermined pressure, duration, and frequency can be delivered to the target surface by the programmed operation sequence of the various control components for the pneumatic delivery line controlled by drive signals received from the controller 30. For example, the delivery of air pulses can be initiated and stopped by pre-designated user control elements on the user interface of the computing device (which can be activated by the user using an input device such as a mouse or keyboard of the computing device 400). For the convenience of the user/operator, the delivery of air pulses can also be initiated by the user's pressing of a foot pedal (not shown in FIG. 3) which can be operatively connected to the controller 30 (which has been programmed to receive and respond to trigger signals from the foot pedal). Two foot pedal configuration, one for initiating the delivery of air pulses and one for stopping the delivery of air pulses, can also be used. For determining a sensory threshold of a tissue, a series of air pulses of varying pressures can be delivered sequentially and automatically to the tissue. For example, the air pulses can be administered with gradually decreasing pressures according to a preset schedule (e.g., the pressures are reduced from 10 mm Hg to 1 mm Hg (spaced by 1 mm Hg), 10 pulses at each pressure, at a duration of 50 ms per pulse and a frequency of 3 seconds per pulse). The sensory threshold can be determined to be between the pressure at which a tissue response is last observed and the pressure at which the tissue response is no longer observable.

Before the system is used to measure sensory response of a patient, the pressure of the air pulses can be calibrated by placing a pneumatic pressure sensor at a predetermined distance corresponding to the required distance between the endoscope tip to the target tissue surface in the contemplated examination condition for the patient. For example, for testing the patient for determining the patient's sensory threshold of the pharyngeal reflex, the operating distance range can be about 8 mm to about 10 mm, therefore for the calibration the pressure sensor is also placed at a distance from the distal end of the endoscope within this distance range. As the pressure regulator 340 is controlled by the controller 30 via drive signals proportional to the voltage provided by the controller, the calibration process can generate a table that correspond between the actual pressures sensed by the pressure sensor and the operating voltage of the pressure regulator 340 provided by the controller 30. This voltage-pressure correspondence can be stored in a storage device of the computing device to be used as operating parameters by the follow-on automatic administration of air pulses of varying pressures in an actual examination of a patient, as discussed above.

Figure 4A:
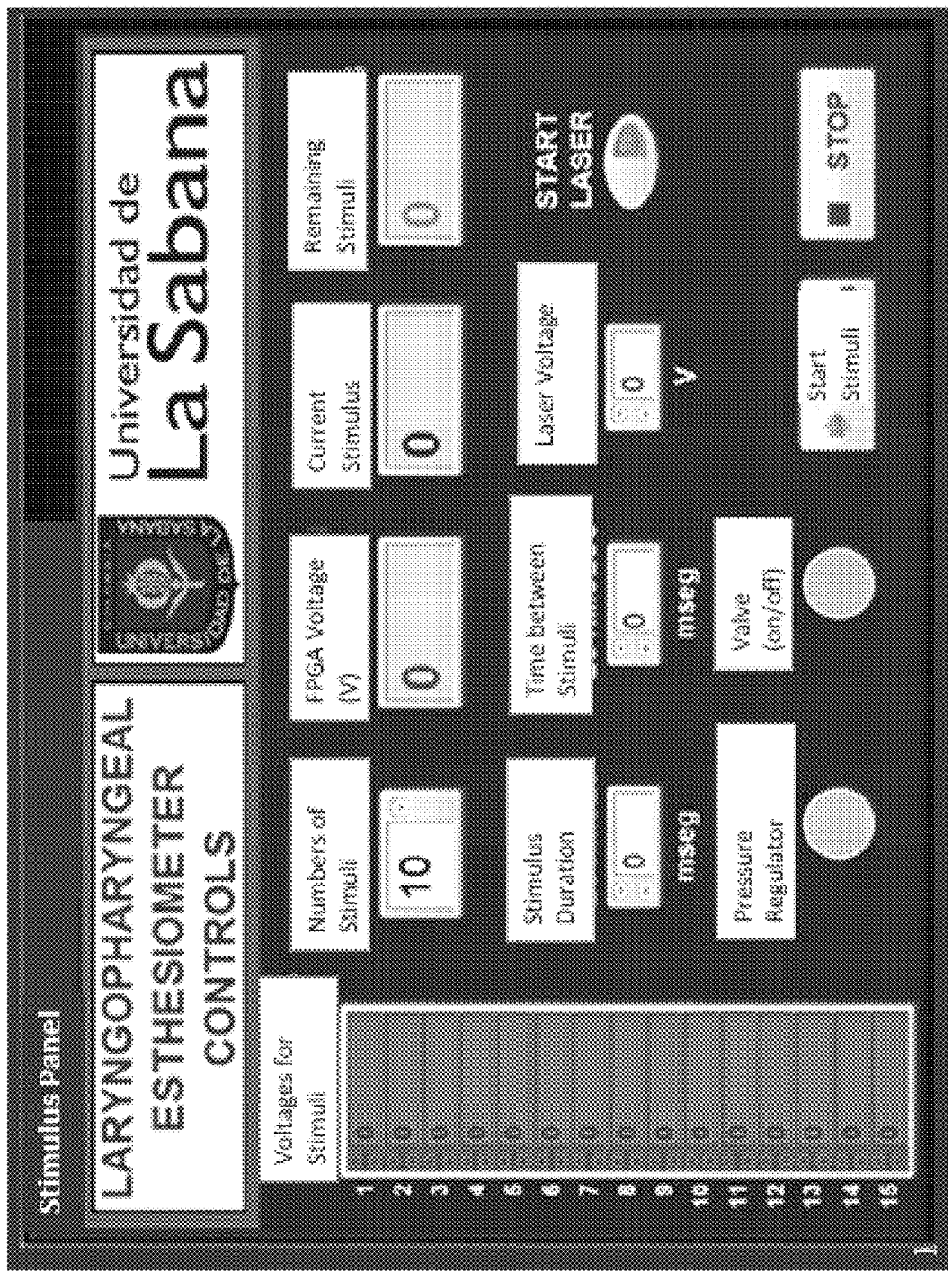
FIGS. 4A and 4B schematically illustrate a user interface for controlling the delivery of air pulses, according to one embodiment of the present invention.
Figure 4B:
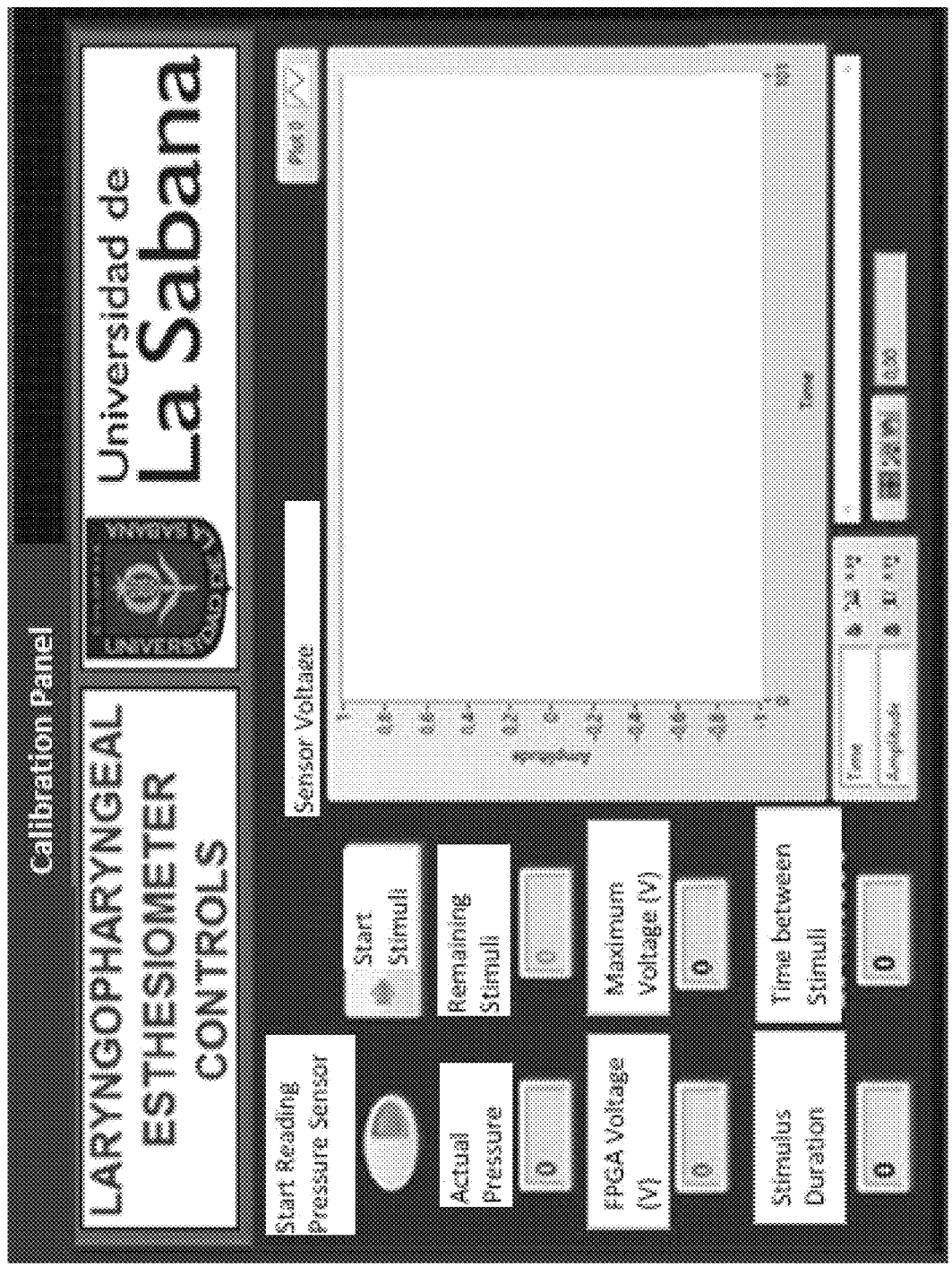

FIGS. 4A and 4B are screenshots of an example user interface as shown on the display of the computing device for configuring and calibrating the air pulses exiting from the distal end of the endoscope. The two screen shots represent two interfaces of a front panel of a software application residing on the memory of the computing device, which can be accessed through the tabs at the top of the application window.

The tab "STIMULUS PANEL" (shown in FIG. 4A) allows the user to enter the parameters required for the generation and display of stimuli (or pulses). The various control and indicator elements shown in FIG. 4A are explained as follows.
Controls:
VOLTAGE FOR STIMULI (V): Through this control the user can set the voltage level sent to the pressure valve, which establishes the degree of opening of the regulator valve to result in a higher or lower output pressure, as required by the user. The number of input boxes (shown as 1 to 15) for the voltage is defined by the control: "NUMBER OF STIMULI". Each box accepts a value between 0 and 10. The default value is 0.

NUMBER OF STIMULI: Through this control, which has a menu of options, a user can select a value between 1 and 15. This value will enable the number of input boxes in the "VOLTAGE FOR STIMULI (V)". The default value for this control is 10.

STIMULUS DURATION: Through this control the user can enter the number of milliseconds for the solenoid valve to remain open for each air pulse. This control allows a value between 0 and 3000. The default value is 100.

TIME BETWEEN STIMULI: Through this control the user can enter the number of milliseconds for the solenoid valve to remain off until the next stimulus is delivered. This control allows a value between 0 and 3000. The default value is 100.

LASER VOLTAGE: Through this control the user enters the voltage level for the laser generator to increase or decrease the power of its beam.

LASER START: Through this control the user activates the laser. In other words, it will turn on or off the laser generator (laser diode). This control is a boolean type, and is activated by clicking on the corresponding button, the color of which can be change, e.g., from yellow to green, when activated.

START STIMULI: Activating this control will start the delivery of the stimuli sequence configured with previously defined parameters. The pressure level will depend on the values in the control: "VOLTAGE FOR stimuli (V)", each stimulus will last according to the "STIMULUS DURATION" and the frequency will depend on the "TIME BETWEEN STIMULI" value. This control is a boolean type, and is activated by clicking on the corresponding button, the color of which can change, e.g., from yellow to green, when activated.

STOP: Through this control the user can stop the delivery of air pulses. This control is a boolean type, and is activated clicking on the corresponding button, the color of which can change, e.g., from yellow to green, when activated.
Indicators:
FPGA VOLTAGE (V): This indicator allows the user to see what level of voltage is being sent to the pressure regulator during the generation of each stimulus. The data shown in this indicator corresponds to each of the values set in the control "VOLTAGE FOR STIMULI (V)", as previously configured.

CURRENT STIMULUS: This indicator shows the number of the stimuli running at any particular moment. This number of stimuli corresponds to the number of the stimuli set at the "VOLTAGE FOR STIMULI (V)" control.

STIMULI REMAINING: This indicator shows how many stimuli are remaining to complete the series previously configured.

PRESSURE REGULATOR: This indicator shows when the pressure regulator is receiving the voltage showed at "FPGA VOLTAGE (V)". This is a boolean indicator and its color can change, e.g., from yellow to green, when activated.

VALVE ON/OFF: This indicator shows when the solenoid valve is open or closed. This is a boolean indicator and its color can change, e.g., from yellow to green, when activated.

The tab "CALIBRATION PANEL" (shown in FIG. 4B) allows the user to activate the display and writing of the data coming from the pressure sensor (MPX2010GSX). The various control and indicator elements on this panel are shown in FIG. 4B and explained as follows.

Controls:

START READING PRESSURE SENSOR: This control enables the reading and writing of pressure data coming from the pressure sensor (e.g., the MPX2010GSX sensor in the embodiment described herein). It allows the user to capture this signal from the sensor for it to be displayed and/or written in an output file, e.g., text file, or a spreadsheet file, which is stored in the local memory of the computing device.

STIMULI START: This control has the same meaning and functionality as the "Stimuli Start" control explained above in connection with FIG. 4A.

Indicators:

MAX VOLTAGE: This indicator shows the maximum voltage recorded by the pressure sensor during each reading.

SENSOR VOLTAGE: This graph indicator shows the user, in real time, the values captured by the pressure sensor in a voltage vs time plot.

The indicators FPGA VOLTAGE (V), CURRENT STIMULUS, STIMULI REMAINING, STIMULUS DURATION, and TIME BETWEEN STIMULI each have the same meaning and functionalities of the corresponding controls as explained above in connection with FIG. 4A.

As described above, the proper positioning of the distal end of the endoscope relative to the target surface is a critical factor for the accuracy and reliability of the sensory threshold test based on air pulses delivered from the distal end of the endoscope. To determine whether the endoscope is being positioned (and maintained) at the desired distance, the present invention provides a software component or module on the computing device 400 for distance calibration and estimation, which is explained as follows.

Distance Calibration:

In this module, the objective is to obtain a table with the measured distance (dc) between the distal end of the endoscope and a surface where the laser spot is projected (this measurement can be made with a high precision micrometer from the distal end of the endoscope to a test surface). This measured distance was compared with the distance between the center of the laser spot (spot center of mass) and the center of the visual field of the image captured by the camera capture component of the endoscope. This distance on the digital image is referred to as radius (r). The relation between "dc" and "r" was then plotted in a scatter plot and different regressions (such as linear regression, higher-powered polynomial regressions or other types of regressions) were performed to find a correlation between the two variables. The goodness of fit of the regression equations was evaluated by the coefficient of determination ($R^2$). In one embodiment, it was found that the best regression equation was an exponential one, e.g., r=A*exp (B*dc), where the constants A, B and C obtained by boundary conditions selected experimentally.

Distance Estimation:

In this module, the reverse relationship between r and dc as determined in the calibration can be used to derive the distance from the distal end of the endoscope to a tissue surface of a patient, based on the distance from the center of the laser spot on the image captured by the endoscopic image capture component relative to the center of the visual field of the endoscopic image capture component. For example, if the above exponential equation is used, the estimated distance can be obtained by d=ln(r/A)/B. The distance estimated can be directly (numerically) shown on the user interface of the display of the computing device 400. Alternatively, and in one embodiment, the above exponential equation can be used to plot a polar grid with circles.

Figure 5:
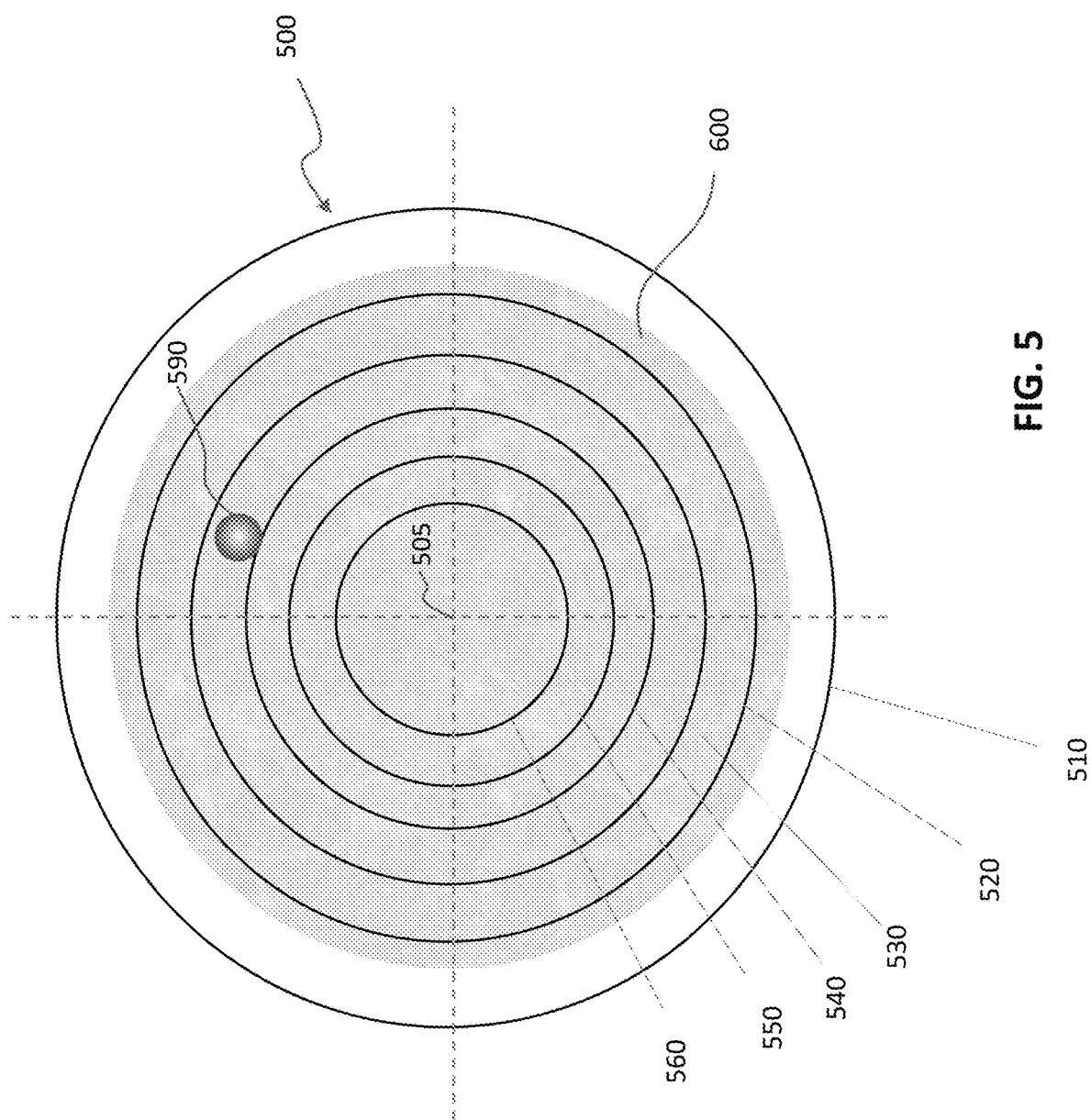
FIG. 5 illustrates a polar grid by which the distance between the distal end of an endoscope and the target tissue surface can be obtained, according to one embodiment of the present invention.

As shown in FIG. 5, the polar grid 500 can be superimposed onto the real time image 600 captured for the target tissue surface (the center 505 of the polar grid 500 coincides with the center of the image capture component of the endoscope), where the circles on the polar grid can be used to indicate to the user the estimated distances to allow the user to conveniently see the estimated distance based on where the laser spot 590 visually falls within the polar grid while making visual inspection of the tissue surface. For example, in one embodiment and as shown in FIG. 5, the circles 510, 520, 530, 540, 550, and 560 represent the estimated distances of 1.78 mm, 3 mm, 6 mm, 9 mm, 12 mm and 15 mm, respectively. The outmost circle 510 indicates the shortest distance and can be used to center the image capture component before starting an actual test. Additional circles can be plotted by interpolating between these circles using the regression equation obtained from the calibration. An additional cross can also be plotted covering the entire visual field with its center at the center of the visual field to help locating the endoscope in the correct place of the body tract or cavity. In the distance estimation, the position of the laser spot can be performed by digital graphics processing techniques, which can include segmentation of the laser spot from the background (e.g., by color and/or intensity analysis of the image) and determining the center of the laser spot.

The scope of the present invention is not limited by what has been specifically shown and described hereinabove. While certain embodiments of the present invention have been shown and described, it will be obvious to those skilled in the art that changes and modifications may be made without departing from the spirit and scope of the invention. The matter set forth in the foregoing description and accompanying drawings is offered by way of illustration only and not as a limitation.

What is claimed is:

1. A system for measuring a sensory discrimination threshold of a tissue of a body cavity of a subject, the system comprising:
   an endoscope operatively coupled to a controller, and the controller operatively coupled to a computing device, the endoscope having
      a body portion;
      a port located on the body portion, the port adapted to receive fluid from an external fluid source;
      a tubular portion connected to the body portion, the tubular portion having a distal end, the distal end being adapted to be inserted into a body cavity of a subject and to be positioned near a tissue of the subject; and
      a range finder component comprising an image capture component configured to capture an image of the selected area of the surface of the tissue and a laser emitting component configured to project a laser light onto a target location in a selected area of the surface of the tissue, wherein the range finder component obtains images of the surface of the tissue and determines a distance from the distal end of the endoscope to the surface of the tissue;
   wherein the body portion and tubular portion include a working channel passing through the body portion and through the tubular portion, the working channel is disposed between the port on the body portion and an opening located on the distal end of the tubular portion,
   the working channel carrying fluid from the port to the opening and delivering the fluid to a surface of the tissue; the controller comprising
- a pressure regulator and a fast on/off solenoid valve serially coupled to a fluid supply line that connects the external fluid source to the port of the endoscope, the pressure regulator and the fast on/off solenoid valve adapted to generate and deliver fluid pulses to the working channel;
- a pressure sensor measuring a pressure of the fluid exiting from the distal end of the working channel; and
- a laser generator which transmits the laser light through the laser emitting component of the range finder to the distal end of the endoscope;

the computing device comprising a display, a processor and a non-transitory computer readable medium storing instructions, which when executed by the processor, provides a user interface on the display, wherein one or more control elements allow a user to enter one or more parameters as control commands to be sent to the controller.

2. The system according to claim 1, further comprising a lighting component configured to illuminate a selected area of the surface of the tissue, wherein the lighting component comprises a lens disposed at the distal end of the endoscope and a fiber optic connecting the lens to a remotely disposed illumination light source.

3. The system according to claim 1, wherein the image capture component comprises:
- a lens disposed at the distal end of the endoscope;
- a remotely disposed image sensor; and
- a fiber optic connecting the lens and the image sensor, the fiber optic adapted to transmit optical signals received by the lens to the image sensor, wherein the image sensor is configured to convert the optical signals into electrical signals.

4. The system according to claim 3, wherein the processor computes the distance from the distal end of the endoscope to the surface of the tissue by:
- constructing a digital image based on the electric signals generated by the image sensor, the digital image having a visual field having a first center;
- identifying a laser spot in the digital image produced by the laser light projected onto the target location, the laser spot having a second center;
- calculating a determined distance on the digital image from the first center of the visual field to a second center of the laser spot; and
- based on the determined distance, deriving the distance from the distal end of the endoscope to the surface of the tissue.

5. The system according to claim 4, wherein deriving the distance comprises using a regression equation obtained from a prior calibration which correlates a position of a laser spot as shown in an image taken by the image capture component of the endoscope and a measured distance from the distal end of the endoscope to a test surface.

6. The system according to claim 1, wherein the laser emitting component comprises a fiber optic adapted to transmit a laser light from a remotely disposed laser generator.

7. The system according to claim 6, wherein the fiber optic is disposed in a second channel of the endoscope different from the working channel.

8. The system according to claim 1, wherein the fluid is air, and wherein the controller is further adapted to control a pressure of the air supplied into the working channel by controlling the pressure regulator.

9. The system according to claim 8, wherein the controller is further adapted to control a duration of a flow of air entering into the working channel by controlling an open status of the fast on/off solenoid valve.

10. The system according to claim 1, wherein the fluid is air, the system further comprising a buffer air tank coupled to the fluid supply line at a location upstream of the pressure regulator.

11. The system according to claim 10, further comprising a manometer coupled to the fluid supply line at a location upstream of the buffer air tank, the manometer controlling a pressure of air entering into the buffer air tank.

12. The system according to claim 1, wherein the one or more control elements are adapted to allow a user to enter parameters of the controller for controlling the pressure regulator and the fast on/off solenoid valve.

13. The system according to claim 1, wherein the pressure sensor is operatively coupled with the controller and adapted to output a measured pressure to the controller, and wherein the user interface is further adapted to display the measured pressure.

14. The system according to claim 1, wherein the operations further include:
- controlling the pressure regulator and the fast on/off solenoid valve to deliver a plurality of fluid pulses having predetermined pressures, durations, and frequencies to the surface of the tissue according to a preset schedule.

15. A method of measuring a sensory discrimination threshold of a tissue of a body cavity of a subject using the system from claim 1, the method comprising:
- inserting the distal end of the endoscope into the body cavity of the subject and causing the distal end to approach a target location of the surface of the tissue;
- using the computing device, and based on the images acquired by the image capture element of the surface of the tissue, calculating one or more distances between the distal end of the endoscope and the target location of the surface of the tissue, and determining whether the distal end of the endoscope is within a predetermined distance range from the target location of the surface of the tissue;
- based on the one or more distances, positioning the distal end of the endoscope at a selected distance from the target location, the selected distance being within the predetermined distance range;
- by means of the controller, delivering air pulses at varying controlled pressures, durations, and frequencies through the working channel of the endoscope to the target location of the surface of the tissue; and
- based on the response of the tissue to the air pulses, determining a sensory discrimination threshold of the tissue.

16. The method according to claim 15, wherein the processor performs operations including:
- displaying a user interface on the display, the user interface including one or more control elements adapted to allow a user to enter one or more parameters as control commands to be sent to the controller.

17. The method according to claim 16, further comprising:
- before inserting the distal end of the endoscope into the patient, calibrating a pressure of the air to be delivered using a pressure sensor placed at a second selected distance from the distal end of the endoscope, the second selected distance being within the predetermined distance range.

18. The method according to claim 17, wherein the calibrating comprises obtaining a correspondence between a second pressure as measured by the pressure sensor and a voltage required by the pressure regulator to produce the second pressure measured by the pressure sensor.

19. The method according to claim 16, wherein the tissue of the body cavity is a portion of an airway of the subject.

20. The method according to claim 19, wherein the tissue is one of a pharyngeal portion of the airway, a laryngopharyngeal portion of the airway, and a nasopharyngeal portion of the airway of the subject.

21. The method according to claim 19, wherein the tissue of the body cavity is a portion of a digestive tract of the subject.

22. The method according to claim 15, wherein the image capture component comprises:
a lens disposed at the distal end of the endoscope;
a remotely disposed image sensor; and
a fiber optic connecting the lens and the remotely disposed image sensor, the fiber optic adapted to transmit optical signals received by the lens to the remotely disposed image sensor;
wherein the remotely disposed image sensor is configured to convert the optical signals into electrical signals.

23. The method according to claim 22, wherein calculating the one or more distances between the distal end of the endoscope and the target location comprises:
constructing a digital image based on the electric signals generated by the image sensor, the digital image having a visual field having a first center;
identifying a laser spot in the digital image produced by the laser light projected onto the target location, the laser spot having a second center;
calculating a determined distance on the digital image from the first center of the visual field to the second center of the laser spot; and
based on the determined distance, deriving a one or more distances from the distal end of the endoscope to the target location.

24. The method according to claim 23, wherein the deriving the one or more distances comprises using a regression equation obtained from a prior calibration which correlates a_position of a laser spot as shown in an image taken by the image capture component of the endoscope and a measured distance from the end of the endoscope to a test surface.

25. The system according to claim 1, wherein the computer readable medium further stores instructions, which when executed, cause the processor to display a polar grid on a display of the computing device, the polar grid including circularly arranged scales indicating estimated distances from the distal end of the endoscope to the surface of the tissue.

26. A system for measuring a sensory discrimination threshold of a tissue of a body cavity of a subject, comprising:
an endoscope having a distal end, the endoscope comprising
a working channel for delivering air pulses from the distal end of the endoscope to a surface of a tissue of a subject;
an inlet port, in fluidic connection with the working channel, for receiving air from an external air source into the working channel;
a range finder component configured to capture images of the surface of the tissue of the subject for determining a distance from the distal end of the endoscope to the surface of the tissue;
an air flow system comprising
a manometer coupled to the inlet port;
an air tank coupled to the manometer, and
a controller operatively coupled to the endoscope comprising
a pressure regulator in fluidic connection to the air tank;
a fast on/off solenoid valve serially coupled to the pressure
regulator, the fast on/off solenoid valve being adapted to generate air pulses delivered to the working channel,
wherein the controller controls each of the pressure regulator and the fast on/off solenoid valve, and is adapted to cause the pressure regulator and the fast on/off solenoid valve to generate and deliver to the surface of the tissue a series of air pulses having a pressure that varies in accordance with a predetermined schedule, the series of air pulses being adapted to measure one or more sensory thresholds.

* * * * *